United States Patent

Kidd

[11] Patent Number: 5,746,201
[45] Date of Patent: May 5, 1998

[54] CPAP NOSE MASK

[75] Inventor: Lisa A. Kidd, Leawood, Kans.

[73] Assignee: Nellcor Puritan-Bennett, Pleasanton, Calif.

[21] Appl. No.: 786,886

[22] Filed: Jan. 23, 1997

[51] Int. Cl.$^6$ .......................................................... A62B 7/00
[52] U.S. Cl. .................... 128/206.24; 128/207.13; 128/205.25
[58] Field of Search ................ 128/207.13, 206.21, 128/206.24, 204.18, 204.23, 205.25, 206.18, 206.17

[56] References Cited

U.S. PATENT DOCUMENTS

| | | | |
|---|---|---|---|
| D. 322,318 | 12/1991 | Sullivan | 128/207.18 |
| 1,486,290 | 3/1924 | Littauer | 128/207.13 |
| 4,328,797 | 5/1982 | Rollins, III et al. | 128/206.24 |
| 4,414,973 | 11/1983 | Matheson et al. | 128/206.24 |
| 4,803,981 | 2/1989 | Vickery | 128/206.24 |
| 4,846,170 | 7/1989 | McAnalley et al. | 128/207.13 |
| 5,060,655 | 10/1991 | Rudolph | 128/716 |
| 5,159,938 | 11/1992 | Laughlin | 128/858 |
| 5,265,595 | 11/1993 | Rudolph | 128/204.18 |
| 5,267,557 | 12/1993 | Her-Mou | 128/206.21 |
| 5,538,000 | 7/1996 | Rudolph | 128/205.25 |
| 5,657,752 | 8/1997 | Landis et al. | 128/206.18 |

FOREIGN PATENT DOCUMENTS

| | | | |
|---|---|---|---|
| 567 965 | 1/1933 | Germany | 128/206.24 |
| 848215 | 9/1960 | United Kingdom | 128/206.24 |
| 2045091 | 10/1980 | United Kingdom | 128/206.24 |
| 82/01823 | 6/1982 | WIPO | 128/207.13 |

OTHER PUBLICATIONS

Respironics Inc. brochure re CPAP Mask Options.
Nellcor Puritan Bennett brochure re Companion nasal CPAP vinyl mask.
Respironics Inc. Patient Accessory Guide.

*Primary Examiner*—Aaron J. Lewis
*Assistant Examiner*—V. Srivastava
*Attorney, Agent, or Firm*—Hovey, Williams, Timmons & Collins

[57] ABSTRACT

A comfortable, leak-resistant CPAP nose mask (10) is provided having a soft, resilient, synthetic resin body (12) and an air source connection fitting (14). The body (12) presents an internal nose-receiving cavity (20) as well as a generally triangular nose entrance opening (16) and a spaced, opposed, inhale/exhale opening (18); the openings (16,18) are in communication with the cavity (20). The entrance opening (16) is defined by a circumscribing flange (20) and an inboard, pliable, inwardly extending, sealing lip (32). A metallic, deformable, shape-retaining reinforcing member (42) is secured to the outer surface of the flange (22) and extends over the bridge (24) and sidewall regions (26, 28) of the flange (22). The member (42) can be readily shaped so as to accommodate the shape and contour of the user's nose and face.

6 Claims, 1 Drawing Sheet

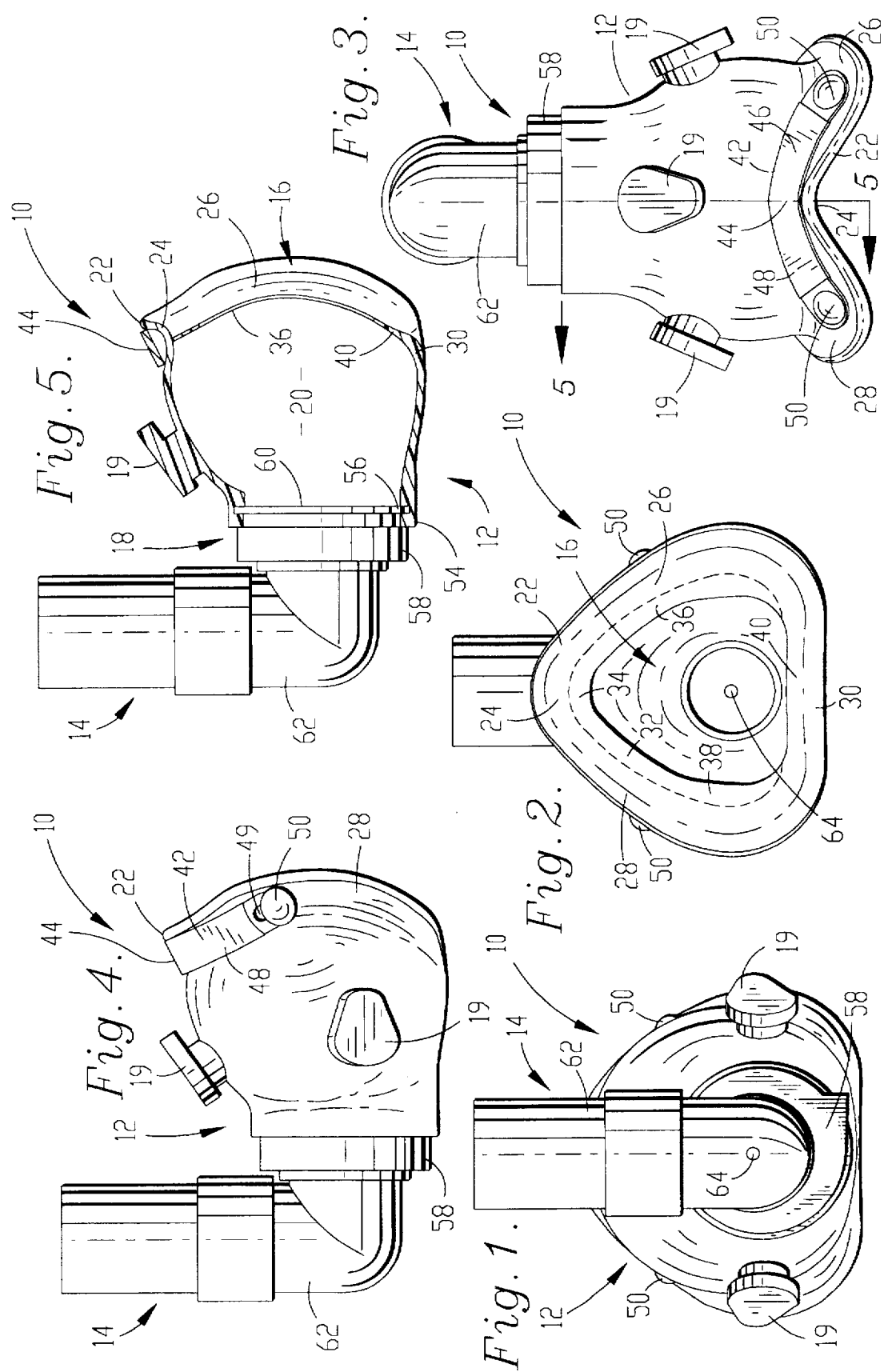

CPAP NOSE MASK

BACKGROUND OF THE INVENTION

1. Field of the Invention

The present invention is broadly concerned with a continuous positive airway pressure (CPAP) nose mask used as a part of sleep therapy for patients suffering from sleep apnea. More particularly, the invention pertains to such a nose mask which is especially configured to maintain positive CPAP pressure by provision of an inwardly extending pliable lip adjacent the nose-receiving opening of the mask, together with an external, metallic, manually deformable, shape-retaining reinforcing bridge element allowing custom shaping of the upper margin of the nose mask to fit the particular nose configuration of the user.

2. Description of the Prior Art

In recent years, CPAP therapy has become a common prescription for individuals suffering from sleep apnea. Such therapy involves placement of a nose or face mask on the patient during sleeping, while positive pressure air is continuously delivered to the patient through the mask. It has been found that this materially lessens the incidents and severity of sleep apnea, thereby allowing the patient to sleep and rest undisturbed.

A common problem encountered with prior CPAP nose masks is the tendency to leak positive pressure air around the bridge and sides of the patient's nose, particularly where the cheek regions and nose intersect. This is undesirable because the continuously leaking positive pressure air tends to dry the patient's eyes, creating uncomfortable wearing and operating conditions. One way of avoiding this problem would be a tighter compressive fit of the nose mask against the nose and face of the wearer. However, the mask cannot be applied with such compressive force as to cause discomfort. Therefore, the designer is faced with the dilemma with on the one hand of providing a comfortable mask, while on the other assuring that positive air pressure leakage is minimized.

SUMMARY OF THE INVENTION

The present invention overcomes the problems outlined above and provides a very comfortable, yet leakage-resistant nose mask which can be readily adapted to the nose and face of virtually any patient. The nose mask of the invention is in the form of a hollow body (preferably of integral construction and formed of a synthetic resin such as silicone rubber) including wall structure defining an internal nose-receiving cavity, a nose entrance opening and a space inhale/exhale opening, with the openings in communication with the cavity. The nose entrance opening is defined by a peripheral flange designed to directly engage the top of the patient's nose, the sides of the nose and cheek regions adjacent the nose, and the patient's upper lip beneath the nose.

In order to provide maximum comfort coupled with low air leakage, the preferred mask also includes a thin pliable lip inboard of the flange and extending into the nose entrance opening. This lip is configured to facilitate a seal between the mask body in order to minimize leakage of positive pressure gas. Advantageously, the nose entrance opening is generally triangular in configuration with the peripheral flange and lip each presenting an upper bridge portion, diverging sidewall portions, and a lower base portion. It has been found that optimum air leakage is provided through the use of a thin inwardly extending lip which is more pliable along the sidewall portions thereof than at the lower base of the lip. In practice, positive pressure air acts against the inner face of the pliable lip to effect the desirable seal of the mask body to the nose and face of the user. At the same time, this pliable sealing lip does not adversely affect the comfort of the mask.

In further preferred forms, the mask of the invention includes a metallic, manually deformable yet shape-retaining reinforcing member secured to the outer surface of the flange remote from the entrance opening. This reinforcing member is generally in the form of a strip and is located for extending over the bridge of the patient's nose and diverging downwardly along both sides of the nose. The user can readily manipulate and deform the reinforcing member for shaping the nose mask around the upper part of the nose and cheeks.

The inhale/exhale opening of the nose mask is located in opposed relationship to the nose entrance opening and receives a fitting allowing connection of a positive pressure air source to the nose mask.

BRIEF DESCRIPTION OF THE DRAWINGS

FIG. 1 is a an end view of the preferred CPAP nose mask of the invention, illustrating the mask and air source fitting;

FIG. 2 is a view similar to that of FIG. 1, but depicting the opposite end of the nose mask and showing in detail the nose entrance opening;

FIG. 3 is a plan view of the preferred nose mask and air source fitting;

FIG. 4 is a side view of the preferred nose mask and fitting; and

FIG. 5 is a sectional view taken along line 5—5 of FIG. 3 and illustrating in detail the configuration of the nose mask assembly.

DETAILED DESCRIPTION OF THE PREFERRED EMBODIMENT

Turning now to the drawings, and particularly FIGS. 1–4, a CPAP nose mask 10 in accordance with the invention is illustrated. The mask 10 includes an integral, molded, synthetic resin mask body 12 together with an interfitted positive pressure air source fitting 14. The mask 10 is designed to fit over the nose of a CPAP patient and be maintained in place during sleep.

In more detail, the mask body 12 is preferably hollow and formed of a pliable synthetic resin material such as silicone rubber. The mask body 12 presents a somewhat triangular nose entrance opening 16 as well as an opposed inhale/exhale opening 18, the latter receiving fitting 14. A nose-receiving cavity 20 is defined by the body 12 and communicates with the openings 16,18. The exterior surface of body 12 is also equipped with three spaced apart connection lugs 19 for connection of head straps allowing secure placement of the mask 10 on a patient's face.

As best seen in FIGS. 2 and 5, the entrance opening 16 is defined by a continuous pliable peripheral flange 22 having an uppermost bridge region 24, downwardly diverging sidewall portions 26, 28 and a concave base portion 30. The flange 22 is designed to conform to the bridge and sides of the patient's nose and to the cheek regions adjacent the nose; in addition, the base portion 30 is designed to abut and engage the upper lip directly beneath the nose. The flange 22 at the upper bridge region 20 preferably has a width of approximately 0.2" and the sidewall portions 26, 28 gradually increase in width until they reach a maximum width of about 0.4" adjacent the base portion 30. The side flange portions 26, 28 then merge into and form the concave base portion 30 having a reduced vertical height of about 0.2".

The entrance opening 16 additionally includes a thin, pliable, continuous lip 32 inboard of the flange 22 and extending into the opening 16. The lip 32 has an uppermost bridge region 34 as well as diverging sidewall portions 36, 38 and a base portion 40. The region 34 and portions 36, 38 of the lip 32 have a width of approximately 0.1" and at the lower ends of the portions 36, 38 merge into the base portion 40 having a similar vertical height of around 0.1". The region 34 and sidewall portions 36, 38 of the lip 32 are relatively thin and flexible, and are thinner than the adjacent portions of the flange 22. The lower base portion 40 of the lip 32 is in effect a continuation of the base portion 30 of the flange 22, and has a thickness essentially equal to that of the flange.

As best seen in FIGS. 3 and 5, the mask body 12 is also equipped with a metallic, manually deformable, shape-retaining reinforcing member 42 secured to the outer surface of flange 22 remote from opening 16 and in a location extending over the bridge region 24 and diverging downwardly along the sidewall portions 26, 28. As shown, the member 42 includes an uppermost bridge portion 44 and a pair of diverging legs 46, 48 each having a connection opening 49 therein. The member 42 is releasably secured to mask body 16 by means of a pair of molded locking protrusions 50, 52 on the exterior surfaces of the flange sidewall portions 26, 28; these protrusions fit within the leg openings 49 as shown. The reinforcing member 42 can be manually shaped as necessary to achieve the optimum fit to a patient's nose adjacent the bridge and sides thereof.

The inhale/exhale opening 18 is circular in configuration and defined by a marginal wall 54 presenting an inwardly extending continuous slot 56. As illustrated, the fitting 14 is releasably connected to the body 12 at the region of opening 18. Specifically, the fitting 14 includes a rigid synthetic resin collar 58 presenting a connection flange 60 which is releasably received within slot 56 of mask body 12. A two-piece L-shaped rigid synthetic resin coupler 62 is rotatably received within collar 58. The end of coupler 62 remote from collar 58 is adapted for connection to a positive pressure air line (not shown). The coupler 62 is provided with a small outlet opening 64 as shown.

In use, the mask 12 with fitting 14 in place is positioned over a patient's nose, usually just prior to bed time. In order to maintain the mask 12 in position, conventional head straps (not shown) are passed over the patient's head and connected to the lugs 19. A positive pressure air line is affixed to the end of coupler 62 remote from mask body 12 for delivery of positive pressure air to the nose-receiving cavity 20. During CPAP treatment, positive pressure air is continually delivered to the nose mask 10 at a selected pressure, typically on the order of 10 cm of water. Such continuous positive pressure air has been found to ameliorate the effects of sleep apnea.

In more detail, provision of the flange 22 and lip 32 of the mask body 12 significantly enhances the seal between the mask body 12 and the patient's nose and face. It has been discovered that positive pressure air acts against the inner face of the pliable lip 32 to form a better seal, particularly along the bridge and sides of the patient's nose leading to the cheek regions. As a consequence, the mask 10 inhibits flow of air past the patient's nose which can causing drying of the patient's eyes. In addition, the presence of the reinforcing member 42 allows custom fitting of the mask 10 to the particular shape and contour of the patient's nose. As will be appreciated, the metallic member 42 can be manually bent and deformed as required to insure the most comfortable fit consistent with adequate sealing.

During the patient's breathing, positive pressure is delivered through the fitting 14. Provision of outlet opening 64 assures that the pressure within the confines of cavity 20 does not build up to an unacceptable degree, thereby causing patient discomfort or significant passage of air along the sides and bridge of the patient's nose.

I claim:

1. A nose mask for receiving a patient's nose and engaging the patient's nose and face, said mask comprising a hollow body including wall structure defining an internal nose-receiving cavity, a nose entrance opening and a spaced inhale/exhale opening, said openings in communication with said cavity, said entrance opening-defining structure having a peripheral flange for directly engaging the top of a patient's nose, the sides of the patient's nose and the cheek regions adjacent the nose, and the patient's upper lip area beneath the nose, and a thin, pliable lip inboard of said flange and extending into said nose entrance opening, said lip being configured for facilitating a seal between said mask body and the patient's nose and face to minimize leakage of positive pressure gas from the nose mask, said flange and lip, at the areas thereof engaging the top of the patient's nose and the sides of the patient's nose and the cheek regions adjacent the nose and diverging from each other, said nose entrance opening being generally tria-ngular in configuration, said range and lip each having a pair of oblique, downwardly extending sidewall portions said lip sidewall portions being thinner and more pliable than said flange sidewall portions.

2. The mask of claim 1, said body being integral and formed of pliable synthetic resin material.

3. The mask of claim 1, said inhale/exhale opening being located in opposed relationship to said nose entrance opening, there being a fitting disposed within said inhale/exhale opening for connection of a positive pressure air source to the nose mask.

4. A nose mask for receiving a patient's nose and engaging the patient's nose and face, said mask comprising a hollow body including wall structure defining an internal nose-receiving cavity, a nose entrance opening and a spaced inhale/exhale opening, said openings in communication with said cavity, said entrance opening-defining structure having a peripheral flange for directly engaging the top of a patient's nose, the sides of the patient's nose and the cheek regions adjacent the nose, and the patient's upper lip area beneath the nose, said entrance opening-defining structure also presenting a thin, pliable lip inboard of said flange and extending into said nose entrance opening, and a metallic, manually deformable, shape-retaining reinforcing member secured to the outer surface of said flange remote from said entrance opening and in a location for extending over the bridge of the patient's nose and diverging downwardly along both sides of the nose, said reinforcing member being deformable for shaping said mask around the upper part of the patient's nose, said nose entrance opening being generally triangular in configuration, said flange and lip each having a pair of oblique sidewall portions, said reinforcing member being disposed directly above and having depending segments extending substantially along the length of said lip sidewall portions for manipulation and shaping of the lip sidewall portions during said mask shaping, said lip sidewall portions being thinner and more pliable than said flange sidewall portions.

5. The mask of claim 4, said body being integral and formed of pliable synthetic resin material.

6. The mask of claim 4, said inhale/exhale opening being located in opposed relationship to said nose entrance opening, there being a fitting disposed within said inhale/exhale opening for connection of a positive pressure air source to the nose mask.

* * * * *